United States Patent [19]

Leavens et al.

[11] Patent Number: 4,866,276

[45] Date of Patent: Sep. 12, 1989

[54] METHOD AND APPARATUS FOR NONDESTRUCTIVE ANALYSIS OF SUBSURFACE FEATURES OF MATERIAL

[75] Inventors: William M. Leavens, Seattle; Ronald C. Zentner, Bellevue, both of Wash.; Charles H. Stonecipher, Boston, Mass.

[73] Assignee: The Boeing Company, Seattle, Wash.

[21] Appl. No.: 139,263

[22] Filed: Dec. 29, 1987

[51] Int. Cl.$^4$ .............................................. G01N 21/88
[52] U.S. Cl. .................................. 250/341; 250/342; 250/358.1; 250/360.1; 374/5
[58] Field of Search ............ 250/341, 340, 342, 358.1, 250/359.1, 360.1; 374/5, 124, 126

[56] References Cited

U.S. PATENT DOCUMENTS

| | | | |
|---|---|---|---|
| 3,681,970 | 8/1972 | Wells | 374/5 |
| 3,808,439 | 4/1974 | Renius | 250/341 |
| 4,302,108 | 11/1981 | Timson | 250/341 |
| 4,309,610 | 1/1982 | Hillemeier | 250/342 |
| 4,377,746 | 3/1983 | Kopineck et al. | 250/359.1 |
| 4,593,456 | 6/1986 | Cheung | 250/338.3 |
| 4,644,163 | 2/1987 | Selander | 250/341 |

FOREIGN PATENT DOCUMENTS 0047612  3/1982  European Pat. Off. ............ 250/341

Primary Examiner—Janice A. Howell
Assistant Examiner—William F. Rauchholz
Attorney, Agent, or Firm—Christensen, O'Connor, Johnson & Kindness

[57] ABSTRACT

The present invention is directed to a method and apparatus for nondestructively locating and identifying subsurface features of a material or structure. A thermographic scanner constructed in accordance with the invention includes a heat source passed over the surface of interest at a controlled speed and followed in a fixed, spaced-apart relation by an array of detectors. The heat source produces an enhanced temperature gradient on the surface that is a function of the subsurface features. The detectors respond to the surface temperature and produce an indication of the type of subsurface features present. The scanner is provided with wheels connected to an optical encoder that produces an indication of the scanner's position over the surface. Thus, the output of the optical encoder is used to indicate the location of the scanner and detectors with respect to the surface. In combination, the outputs of the optical decoder and sensors indicate both the type of subsurface feature present and its location with respect to the surface. This information is displayed to the operator in real-time and is available from stored memory for presentation in graphical form.

19 Claims, 4 Drawing Sheets

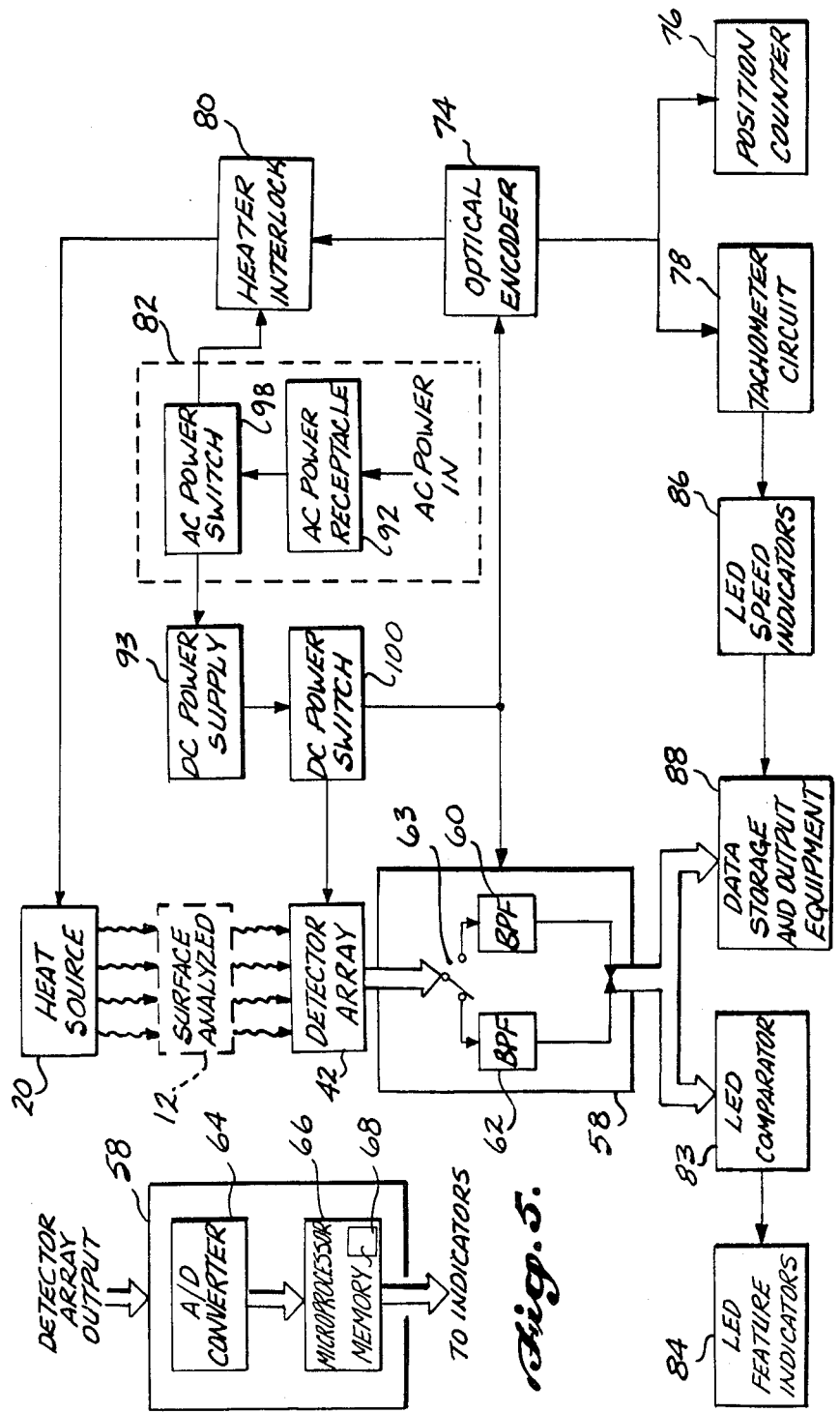

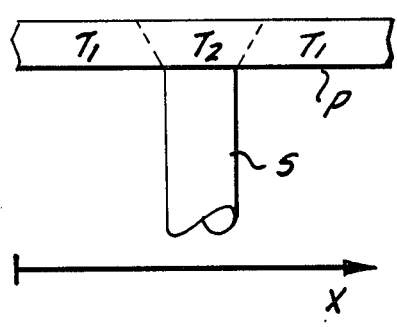 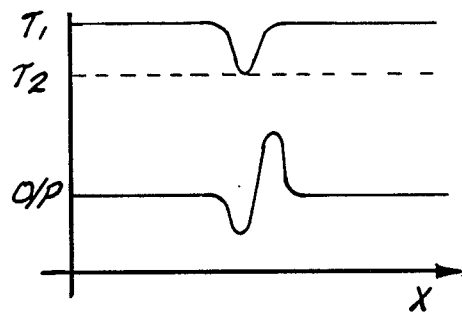
Fig. 6a.  Fig. 6b.
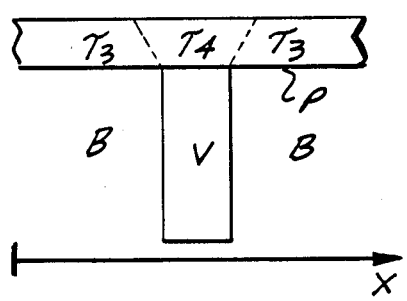 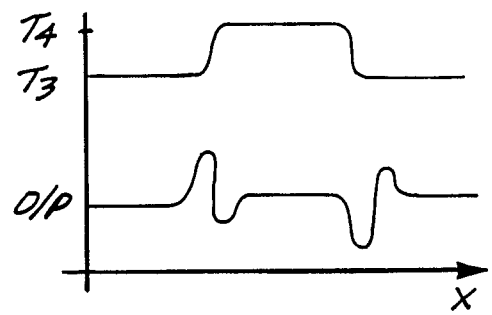
Fig. 7a.  Fig. 7b.
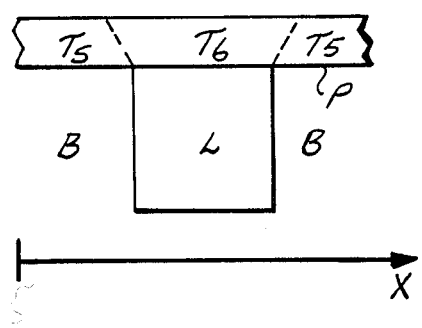 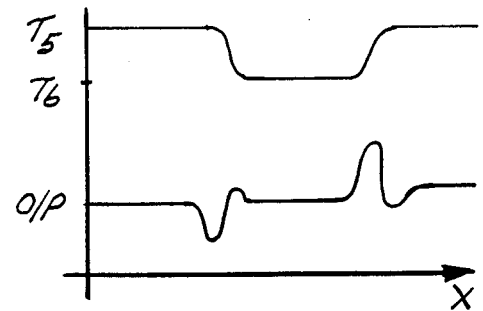
Fig. 8a.  Fig. 8b.

METHOD AND APPARATUS FOR NONDESTRUCTIVE ANALYSIS OF SUBSURFACE FEATURES OF MATERIAL

FIELD OF THE INVENTION

The present invention relates to nondestructive test methods and apparatus and, more particularly, to those methods and apparatus that nondestructively detect and locate near-surface features of a material.

BACKGROUND OF THE INVENTION

The subsurface features of a material or structure are frequently of great importance. For example, voids in metal stock may seriusly affect the strength of the material. Similarly, discontinuities in the bond between adjacent layers of a multilayer structure may impair the strength of the structure. In both cases, subsurface features of the particular object being analyzed ultimately determine the object's utility. Thus, detection of the form, size, and location of the subsurface features is important.

In most instances, direct visual observation of subsurface features requires partial destruction of the material or structure of interest. This method of analysis is often counterproductive, rendering the material or structure analyzed useless. Thus, a nondestructive method of analyzing subsurface features of a material or structure is required.

While a number of nondestructive test methods have been developed, each is subject to certain shortcomings. For example, one method of analyzing the subsurface features of an object involves exposing the object of gamma radiation. Because discontinuities or anomalies below the surface respond differently to radiation, the response of the object to the radiation can be used to identify such subsurface features.

This method of analysis, however, suffers from several disadvantages. First, gamma radiation sources are relatively large, making it impractical to produce a portable test apparatus. Second, a test apparatus responding to the transmission of radiation through an object cannot be used in applications where one side of the region of interest is inaccessible. Third, the use of gamma radiation requires that personnel exposed to the radiation during testing be protected, making the process more expensive and less convenient. In addition, gamma radiation analysis may introduce unwanted levels of radiation in the object that remain after testing.

Another method of nondestructively testing an object for subsurface features involves the use of X-rays. Pursuant to this method, the portion of the object containing the subsurface features of interest is placed between an X-ray source and an X-ray-sensitive film. The surface of the object is then exposed to X-rays. Because the subsurface features influence the X-rays received by the film, the developed film produces an image of the object that can be used to identify the features.

One problem with this method of analysis is that it may be difficult to produce X-rays having enough energy to penetrate many objects to the degree necessary to provide a clear image. For example, the analysis of heavy sheet steel may require a relatively high-energy X-ray source. X-ray analysis also has the disadvantage of requiring that film be placed behind the material or structure to be analyzed. Finally, the process is relatively expensive, particularly when the features beneath a large surface are to be analyzed, because a correspondingly large quantity of film is required.

Ultrasonic test methods have been proposed that overcome some of the problems involved with the use of gamma radiation and X-rays. Ultrasonic analysis involves the exposure of the surface to ultrasonic energy. The response of the object to the excitation is then used to indicate the presence of subsurface features. This method is safer, more convenient, and less expensive than those using gamma radiation and X-rays, but may produce erroneous signals. For example, when the subsurface features of an inspected object include layers of the same or different materials, reflections produced at the interface between the layers may produce an indication of a nonexistent anomaly, such as an air gap.

One nondestructive test method that overcomes these problems is thermography. In principle, thermographic testing involves the exposure of the analyzed surface to even heating. Variations in the thermal conductivity of features below the surface then allow heat to flow away from the surface more rapidly in some places than others, establishing temperature gradients along the surface that provide an indication of the subsurface features of the object. For example, if the structure being examined is made of a material having a relatively high thermal conductivity, like steel, the temperature of the surface will be lower adjacent thicker portions of the material. Similarly, if the material contains voids, the relatively poor conductivity of the air limits heat flow from the surface, resulting in a warm spot on the surface adjacent the void. Thus, temperature patterns on the surface can be used to identify subsurface features.

A number of methods and apparatus have been devised for the nondestructive, thermographic testing of subsurface features. For example, in U.S. Pat. No. 2,260,168 (McNutt), an early form of thermographic testing is illustrated. There, a row of torches acting as a heat source is passed over a metal surface at a uniform speed. While the reference suggests that a plurality of temperature-responsive devices can be positioned following the heat source, in the preferred embodiment the temperature of the heat source is sufficiently high to produce discoloration of the surface adjacent subsurface voids. The arrangement disclosed by McNutt, however, introduces a number of problems. For example, many nonmetallic surfaces may be incapable of producing the requisite discoloration in response to subsurface features. In addition, the relatively high temperatures required to produce discoloration, and thus identify defects, may be destructive when used with many materials. Finally, material analyzed in this manner must be allowed to cool before being handled by test personnel.

A second thermographic test apparatus is illustrated in U.S. Pat. No. 3,206,603 (Mauro). Pursuant to this arrangement, a radiant energy source or induction heating coil supplies heat to the surface of the material being analyzed. As the material being analyzed is passed under the apparatus, infrared energy radiated from its surface is received by an optical system and directed to a rotating chopper mirror, which alternatively reflects the infrared energy to a pair of thermistor bolometers. Thus, the bolometers receive radiation from alternating portions of the surface. A difference in the outputs of the two bolometers indicates a temperature gradient on the surface and thus, the presence of a subsurface anomaly. This arrangement is relatively complex and, when a large portion of the surface is to be analyzed, the use of a single optical path and pair of bolometers requires an inconveniently large displacement between the apparatus and the surface.

A third arrangement for thermographically testing objects is illustrated in U.S. Pat. No. 3,222,917 (Roth). A thermal pulse is applied to a first region of the object under test. A pickup transducer, such as a thermistor, pyroelectric element, or thermocouple, is positioned adjacent a second region of the object. The pickup transducer produces an output dependent upon the transient response of the object to the thermal pulse. The time-dependent amplitude of the response varies if there are flaws present between the region where the thermal pulse was applied and the region adjacent the transducer. This method appears somewhat impractical for use in locating flaws in large objects because the transient response of numerous incremental portions of the object would have to be determined, each taking some time to complete. Thus, inspection of the entire object would be quite time consuming.

A fourth method of thermographic flaw detection is described in U.S. Pat. No. 3,462,602 (Apple). There, rolled sheet steel stock is inspected while it is still hot. A pair of radiometers scan the rolled stock at two spaced-apart locations. The output of each radiometer is a function of the temperature of the surface area viewed. The two outputs are fed to a differential amplifier that produces an output whose magnitude is dependent upon the difference between the two radiometer outputs. Thus, if the temperature of the sheet stock is uniform, the output of the differential amplifier is zero. If the temperature of the two regions viewed by the radiometers is different, however, the differential amplifier produces a nonzero output. a trigger circuit signals the presence of a defect when the output of the differential amplifier exceeds a predetermined level.

There are several disadvantages with the Apple arrangement. First, radiometers must be displaced a relatively large distance from the surface if more than a small point on the surface is to be observed. In addition, two radiometers are required to determine the presence of a flow in one portion of the workpiece. Third, if small defects are to be located in a relatively large object, the distance between the radiometer observation points must be relatively small and a substantial amount of time is required to sweep the entire surface.

In light of the foregoing discussion, it would be desirable to develop a method of, and apparatus for, nondestructively locating and identifying nearsurface features of an object when only one surface of the object is accessible. Such a system should be capable of rapidly locating and identifying relatively small features below the surface. In addition, the apparatus should be compact, relatively simple, and inexpensive.

SUMMARY OF THE INVENTION

In accordance with this invention, an apparatus is provided for locating subsurface features of a material. The apparatus includes detection means, location means, and analyzing means. The detection means is responsive to the temperature of the surface and, when exposed to contiguous surface regions, produces an output that is a function of the temperature of the contiguous regions. The analyzing means, in turn, produces a response when the output of the detection means falls within one of a number of predetermined output ranges corresponding to the various subsurface features to be identified. The location means produces an indication of the longitudinal position of the detection means with respect to a reference point on the surface of the material. This indication is used by the analyzing means to further produce a response that indicates the relative position of the particular feature identified with respect to the reference point on the surface.

In the preferred embodiment, the detection means is a linear array of pyroelectric detectors, which respond directly to changes in the temperature of the surface. The array of detectors is passed over the surface and the detector outputs are applied to a plurality of filters designed to pass signals corresponding to certain subsurface features of interest. An array of light-emitting diodes (LEDs) is also provided on the apparatus, with each LED being aligned above a corresponding detector. The presence of a feature of interest is then indicated by the lighting of those LEDs whose corresponding detector outputs are passed by the filter. In addition, a signal is produced by an optical encoder, allowing the position of the apparatus with respect to the surface to be determined. This information, along with the identity of each defect, is received by means provided for storing and plotting the location and identity of subsurface features for the entire surface.

The preferred embodiment also includes a heat source that is substantially parallel to the linear array of detectors. The heat source is passed in space relation over the surface in front of the detectors, establishing a more easily identifiable temperature gradient on the surface. In this manner, the identification and location of subsurface features is made easier. To prevent overheating of the surface, the apparatus includes means for disabling the heat source when the relative motion between the apparatus and the surface is substantially zero.

In accordance with another aspect of this invention, a method of nondestructively locating and identifying subsurface features of a material is provided. Included in this method is the step of uniformly heating the surface of interest. The temperatures of a plurality of points on the surface are then detected and compared with surface temperature patterns associated with particular types of subsurface features. If the comparison indicates that the temperatures of the plurality of points are within a predetermined range of the temperature patterns associated with one of the feature types, an indication is produced identifying the location and particular type of the feature.

BRIEF DESCRIPTION OF THE DRAWINGS

The invention will presently be described in greater detail, by way of example, with reference to the accompanying drawings, wherein:

FIG. 4 is a block diagram which illustrates a scanner constructed in accordance with the invention;

FIG. 5 is an alternative block diagram of a portion of the scanner diagrammed in FIG. 4;

FIGS. 6a and 6b illustrate a material having a first type of subsurface feature to be detected, the temperature distribution across the material produced by the subsurface feature, and the signal produced by a portion of the scanner in response to the subsurface feature;

FIGS. 7a and 7b illustrate a material having a second type of subsurface feature to be detected, the temperature distribution across the material produced by the subsurface feature, and the signal produced by a portion of the scanner in response to the subsurface feature; and FIGS. 8a and 8b illustrate a material having a third type of subsurface feature to be detected, the temperature distribution across the material produced by the subsurface feature, and the signal produced by a portion of the scanner in response to the subsurface feature.

DESCRIPTION OF THE PREFERRED EMBODIMENT

Figure 1:
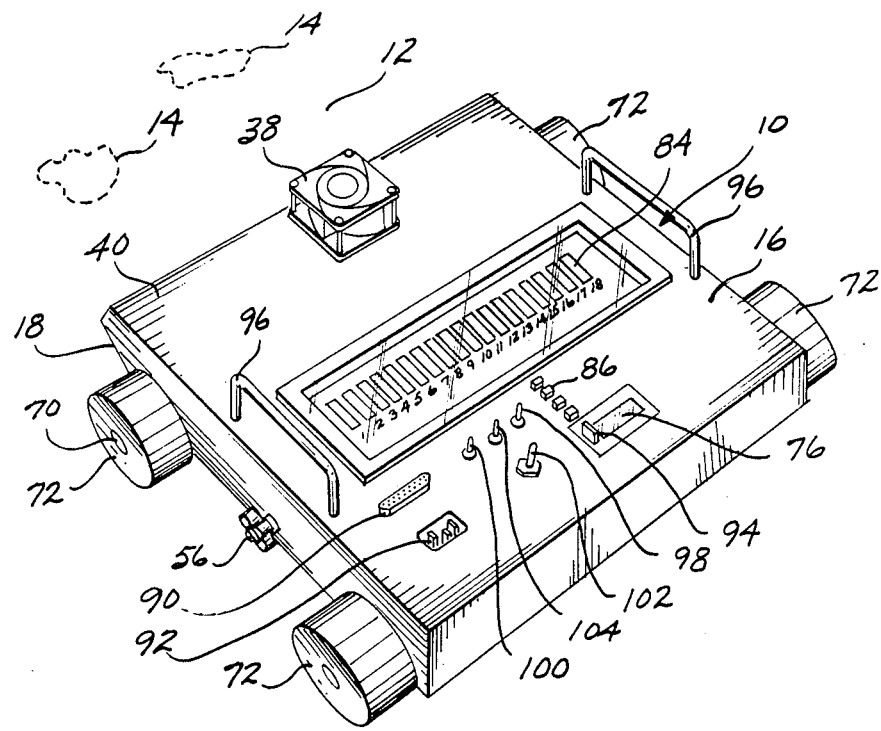
FIG. 1 is a pictorial view of a scanner, constructed in accordance with this invention and used to analyze subsurface features of a material, showing the various operator controls and scanner outputs.

FIG. 1 depicts a preferred embodiment of an apparatus constructed in accordance with this invention. As shown, the apparatus is a portable, hand-held scanner 10 used adjacent a surface 12 having a plurality of subsurface features 14 of interest. These features may include, for example, variations in material thickness and composition, we all as the presence of subsurface voids or cracks. As scanner 10 is moved across surface 12, the identity and location of subsurface features 14 are indicated without deleteriously affecting the integrity of the material being analyzed.

Figure 2:
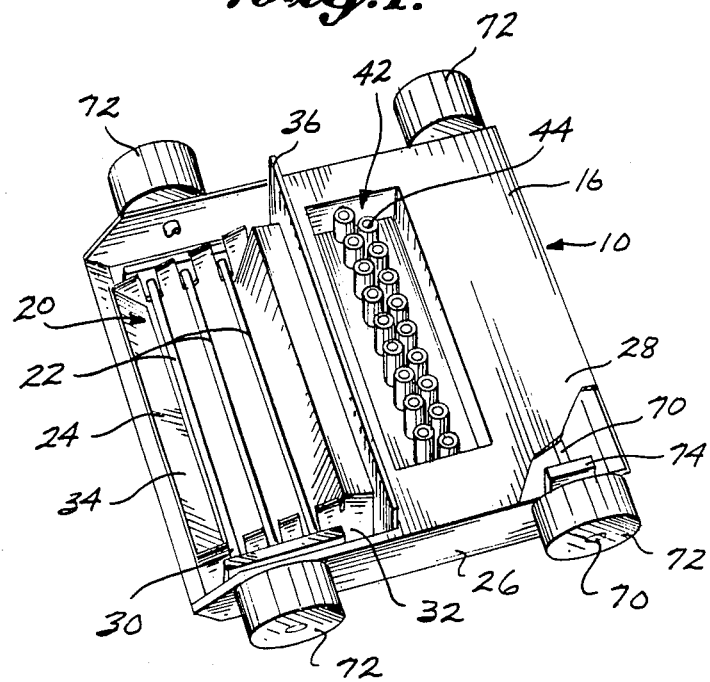
FIG. 2 is a pictorial view of the underside of the scanner illustrated in FIG. 1 showing the heat source and detection devices employed by the scanner.
Figure 3:
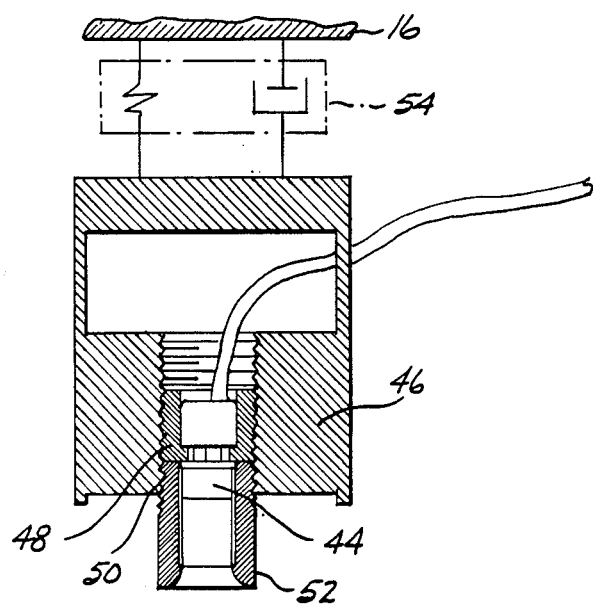
FIG. 3 is an enlarged cross-sectional view of a detection device mounted to the scanner illustrated in FIGS. 1 and 2.

Thermographic scanner 10 will now be considered in greater detail with reference to FIGS. 1, 2 and 3. A housing 16 is the primary structural component of scanner 10 and provides a connection point for the various other scanner components. Housing 16 is preferably made of a lightweight material, for example, sheet aluminum. The overall dimensions of housing 16 are the smallest consistent with the housing's functions of properly positioning and protecting the components of scanner 10. In the preferred embodiment, housing 16 is in the form of a relatively thin, rectangular box. The lower, forward portion 18 of housing 16 is tapered upwardly toward the front of housing 16. As scanner 10 is moved across surface 12, this tapered portion 18 allows scanner 10 to more readily traverse nonplanar surfaces. Otherwise, with scanner 10 used to analyze, for example, a concave surface 12, the forward portion 18 of scanner 10 could contact and interfere with surface 12, making it difficult to move scanner 10 across the surface 12.

The next element of scanner 10 to be considered is a heat source 20, connected to housing 16. Scanner 10 responds to temperature information obtained from surface 12, making use of empirically derived data relating the temperature gradients of surface 12 to the identity of subsurface features 14 of interest. To obtain useful temperature information from surface 12, it is desirable to ensure that the temperature of each point on the surface is a function of only the particular features 14 below surface 12. Otherwise, scanner 10 must also receive inputs corresponding to other variables and compensate for their effect on the feature type indicated.

One such other variable is the amount of heat applied to each portion of surface 12. It is, therefore, preferred that each portion of surface 12 be exposed to the same amount of heat. If the object, structure, or material being analyzed is in an environment having a uniform temperature distribution, this objective is satisfied. Analysis of the temperature of the surface can then be used to identify and locate selected types of features 14 below surface 12.

In some instance, however, the normal environmental temperature of surface 12 is such that the effect of a subsurface feature 14 on the temperature of surface 12 is relatively small in magnitude. In this case, surface temperature patterns are more difficult to detect, making analysis by scanner 10 more difficult. To overcome this problem, heat source 20 is included on scanner 10. As will be considered in greater detail below, heat source 20 provides uniform heat to surface 12, increasing the average temperature of the surface 12, as well as the magnitude of the surface temperature variation produced by a subsurface feature 14.

As shown in FIG. 2, heat source 20 includes three lamps 22 and a reflector 24. The particular lamps 22 selected are a function of a number of considerations. First, the desired magnitude of the effect that a particular subsurface feature 14 is to have on the temperature of surface 12 is determined. Basically, the greater the effect produced by a subsurface feature 14, the more easily and accurately scanner 10 will be able to locate and identify the feature 14. Once the magnitude of the desired effect is known, the requisite heat per unit of surface area to be applied to surface 12 to achieve that effect can be determined.

The heat per unit surface area needed and developed is influenced by a number of factors including the width of heat source 20 in the direction of scanner 10 travel, the preexisting temperature of surface 12, the temperature of source 20, the height of source 20 above surface 12, and the rate of travel of scanner 10 across surface 12. In an application analyzing the subsurface features of a 0.25 inch (0.64 cm) thick steel plate covering fourteen inches (5.52 cm) of concrete, it has been found that the application of approximately 20 BTU/foot$^2$ (22.7 J/cm$^2$) to surface 12 produces surface temperature characteristics that allow subsurface features 14 to be easily identified and located. As shown in FIG. 2, three parallel, equally spaced-apart lamps 22 are employed. These lamps are of the relatively low-intensity, incandescent type and are disposed perpendicularly to the sides 26 of housing 16. Lamps 22 are uniformly spaced from the lower surface 28 of housing 16 and pass through slots 30 provided in the sides 32 of reflector 24 before being connected to a source of power within scanner 10.

As will be apparent from FIG. 2, reflector 24 reflects substantially all of the upwardly directed radiation emitted by lamps 22. The upper section 34 and sides 32 of reflector 24 reflect upwardly and laterally directed radiation from lamps 22 downward to the surface 12 being analyzed. Thus, reflector 24 increases the heating efficiency of the lamps 22, while reducing the amount of heat absorbed by scanner 10.

As shown in FIG. 2, a heat shield 36 is disposed from the lower surface 28 of housing 16 rearward of heat source 20. A variety of configurations for heat shield 36 are acceptable. As shown, however, heat shield 36 is a relatively thin structure arranged to extend within close proximity, or in contact with, surface 12. The function of heat shield 36 is to minimize direct radiation from heat source 20 to the detection circuitry employed in the rearward postion of scanner 10. Heat shield 36 can be made of, for example, plastic sheet and is preferably angled slightly rearwardly from the lower surface 28 of housing 16 to allow it to travel smoothly over anomalies on surface 12.

Although reflector 24 minimizes the amount of heat transferred by lamps 22 to housing 16, a fan 38 is provided on the upper surface 40 of housing 16, adjacent the side of upper reflector section 34 opposite lamps 22. Fan 38 is of the axial type and, when energized, provides forced-air ventilation between the interior of scanner 10 and the external environment of scanner 10. In this manner, heat buildup within scanner 10 resulting from the operation of lamps 22 is minimized. It has been found that for a heat source 20 producing approximately 20 BTU/foot$^2$ (22.7 J/cm$^2$), a fan 38 having an output of 38 feet$^3$/minute (0.79 m$^3$/min) is acceptable.

Although, in the preferred embodiment, a heat source 20, including lamps 22, reflector 24, and heat shield 36 is employed, heat source 20 may be unnecessary for many applications. In addition, different heat sources 20 can be used employing for example, resistive heating units. In addition, heat shields can be provided integrally with the detection circuitry of scanner 10 or, like reflector 24, can be eliminated altogether, depending upon the circuitry employed.

The next element of scanner 10 to be considered is detector array 42, which is recessed in the lower surface 28 of housing 16, rearward of heat source 20. Detector array 42 is responsive to the temperature of surface 12 and the spacing between array 42 and heat source 20 is selected in conjunction with the speed of scanner 10 travel to produce the desired responsivity of array 42 to the temperature of surface 12. Array 42 includes a plurality of pyroelectric detectors 44 downwardly disposed from a base member 46 that is attached to housing 16. The pyroelectric detectors 44 are crystalline in nature and absorb radiation produced by surface 12. This radiation increases the temperature of the crystal, changing the crystal's lattice spacings, as well as the spontaneous electric polarization existing in the crystal. With leads connected to the surfaces of the crystal that are normal to the axis of polarization, a current is generated that is proportional to the rate of change of surface 12 temperature.

While numerous temperature-responsive devices can be employed, pyroelectric detectors 44 are preferred in that they respond directly to the temperature change of surface 12. Their output can then be compared to known thermal gradients associated with particular subsurface features of interest. In addition, pyroelectric detectors 44 are relatively simple, small, and advantageously have low thermal masses, providing faster responses to temperature changes on surface 12. Germanium windows are provided over detectors 44 to reduce noise associated with temperature changes produced by convection or drafts of air across the detector 44. Pyroelectric detectors 44 having the foregoing attributes are available in the P1-series from Molectron Corp. 177 North Wolfe Road, Sunnyvale, Ca 94086, and have a sensitivity response from .005 to 1.00 degrees C.

As shown in FIG. 3, each detector 44 is mounted in an externally threaded, cylindrical detector housing 48. The detector housing 48, in turn, resides in a threaded opening 50 provided in base member 46. In a preferred embodiment, a cylindrical heat shield 52 is additionally threaded into opening 50, extending downwardly from detector 44 and opening toward surface 12. As will be apparent from FIG. 3, the distance that heat shield 52 extends beyond detector 12 controls the aspect ratio of detector 44 with respect to surface 12. For example, with detector 44 positioned a given distance above surface 12, a relatively long heat shield 52 produces a small aspect ratio in which detector 44 "views" a relatively small portion of surface 12. If, on the other hand, heat shield 52 extends only a short distance beyond detector 44, a high-aspect ratio results for a given separation between detector 44 and surface 12 and a relatively large portion of surface 12 is viewed. Thus, heat shield 52 both limits the direct radiation received by detector 44 from heat source 20 and contributes to the resolution of detector array 42, as will be described in greater detail below.

In the preferred embodiment, detector array 42 includes eighteen pyroelectric detectors 44, positioned on base member 46 and arranged in two parallel lines substantially perpendicular to the housing sides 26. The number and spacing of pyroelectric detectors 44, as well as the configuration of heat shields 52, are selected to provide the desired resolution or ability of scanner 10 to identify and locate subsurface features 14. With a relatively large number of closely spaced detectors 44, having relatively small individual aspect ratios, the location of a particular subsurface feature 14 can be precisely identified. With only a few detectors 44 employed, having relatively high individual aspect ratios, however, the location of a particular subsurface feature 14 will be much less precisely indicated.

The output of the various detectors 44 is dependent upon a number of factors. For example, the magnitude of the output signals produced by detectors 44 is inversely proportional to the height of the detectors 44 above surface 12. Thus, each of the detectors 44 in array 42 is displaced a uniform distance from surface 12. The height of the isolated detector array 42 over surface 12 is, however, adjustable by way of the adjustment knobs 56 shown in FIGS. 1 and 2. This allows the entire array 42 to be lowered, increasing both the resolution of detectors 42 and the magnitude of their outputs. When the height of array 42 is increased, however, resolution and detector outputs decrease.

The output of detectors 44 can be undesirably influenced by vibration induced in the detector array 42. For that reason, as shown schematically in FIG. 3, a shock isolation system 54 is provided between base member 46 and housing 16. For example, shock isolation system 54 may consist of a spring-loaded diaphragm to which base member 46 is connected. Shock isolation system 54 provides a resilient, damped connection between base member 46 and housing 16, minimizing the influence of vibration on the output of the various detectors 44.

As shown in FIG. 4, the output of the various detectors 44 in array 42 is input to a signal-conditioning circuit 58. In a preferred embodiment, signal-conditioning circuit 58 includes two separate active band-pass filters 60 and 62 and a two-position switch 63 for each detector 44 output to be conditioned. Thus, while the currently preferred embodiment includes eighteen sets of these components, for convenience, only one set is shown in FIG. 4.

Switch 63 is used to selectively connect the corresponding detector 44 to either filter 60 or filter 62. Filters 60 and 62 are designed to pass those detector 44 signals that exhibit frequencies corresponding to the frequency of detector 44 signals empirically determined to be produced in response to the presence of two distinct types of subsurface features 14. Thus, in the preferred embodiment, with switch 63 connected to filter 60, the output of filter 60 is used to indicate the detection of a first subsurface feature type by a detector 44. Switch 63 can then be used to select filter 62, and surface 12 examined for the presence of a second subsurface feature type.

While active filters are employed in the preferred embodiment to eliminate the need for the relatively heavy inductors required by passive filters, it will be readily appreciated that passive filtering techniques can be employed. Switch 63 could also be omitted and a separate array of LED feature indicators 84 connected to each filter 60 and 62, allowing the various subsurface feature types to be simultaneously detected. To reduce the amount of circuitry involved, two bandpass filters 60 and 62 and a two-position switch 63 could be coupled to each of the detectors 44 by a sequencer (not shown). The sequencer supplies the output of the various detectors 44 to the particular filters selected by switch 63 in a predetermined, repetitive sequence and also provides an indication of which detectors 44 a particular subsurface feature 14 was sensed by. This arrangement, however, has the disadvantage of requiring a longer cycle time for the conditioning of the output of each detector in array 42.

Other means are available to identify detector 44 outputs corresponding to subsurface features 14 of interest. For example, the output of detectors 44 can be input to a signal-conditioning circuit 58 constructed as shown in FIG. 5. The output of each detector 44 is received by analog-to-digital (A/D) converter 64. The output of A/D converter 64 is then analyzed by microprocessor 66, which stores the received signal in memory 68 and compares it with corresponding, empirically derived signals associated with the various subsurface features 14 of interest. Microprocessor 66 produces an output that indicates the particular subsurface features 14 sensed by the various individual detectors 44.

Regardless of the construction of signal-conditioning circuit 58, it will be appreciated that the number of subsurface feature types that the output of detectors 44 are used to identify can be increased or decreased as desired. The output of signal-conditioning circuit 58 directly indicates the type of subsurface feature 14 present and, for illustrative purposes, qualitative representations of the output produced in response to various subsurface structures and their corresponging surface temperature variations are provided in FIGS. 6, 7, and 8.

A subsurface structure including a stud S secured to a lower surface of a metal plate P is shown in FIG. 6a. The remainder of plate P is in direct contact with air. When the upper surface of plate P is exposed to uniformly distributed heat from source 20, it generally exhibits a temperature $T_1$ that is a function of a variety of factors including the amount of heat applied and the thermal characteristics of plate P. Because the stud S has a higher thermal conductivity than the surrounding air, however, it acts as a "sink" drawing heat away from the adjacent portion of plate P and producing a corresponding drop in the surface temperature T of plate P to some level $T_2$.

A curve illustrating the distribution of the temperature T across plate P is shown in FIG. 6b. The detectors 44 respond to the temperature variation experienced adjacent stud S and, provided that the frequency of the signal falls within the passband of the particular filter 60 or 62 selected, the signal-conditioning circuit 58 will produce an output O/P that is proportional to the differential of the detector 44 input. By applying this output O/P to a comparator 83, the transition of O/P above some adjustable, predetermined threshold can be used to trigger an output indicating the detection of stud S.

FIG. 7a illustrates another subsurface feature of interest. As shown, metal plate P is positioned adjacent a solid base B that includes an air pocket or void V next to the lower surface of plate P. In this case, the temperature T at the surface of plate P is predominantly equal to $T_3$. Assuming that the base B has a higher thermal conductivity than the void V, the base B will conduct heat away from plate P more rapidly than void V. As a result, a "hot" spot having a temperature $T_4(T_4>T_3)$ will occur at the surface of plate P adjacent void V.

The temperature distribution across the surface of the plate P shown in FIG. 7a is illustrated in FIG. 7b. With the appropriate filtering selected in signal-conditioning circuit 58, the corresponding output O/P shown in FIG. 7b is produced. with the threshold of comparator 83 correctly established, an output indicating the detection of void V is produced.

The final subsurface structure type to be discussed is illustrated in FIG. 8a. As shown, the metal plate P covers a solid base B having a liquid-filled void L adjacent the plate P. Assuming that the liquid-filled void L has a higher thermal conductivity than base B, it will conduct heat away from the plate P more readily than the base B. As a result, the predominant surface temperature $T_5$ is somewhat higher than the temperature $T_6$ adjacent void L. The distribution of temperature T and corresponding output O/P of signal-conditioning circuit 58 are shown in FIG. 8b.

As will be appreciated from the preceding discussions, numerous factors quantitatively affect the temperature T and output O/P curves characterizing a particular subsurface structure of interest. thus, to properly adjust the scanner 10 to detect, for example, the presence of a stud S, it is helpful to empirically drive the curves T and O/P produced by a particular combination of plate P, stud and scanner 10 set-up. an appropriate passband for filter 60 or 62 can then be selected, along with the threshold for comparator 83 that is required to produce an output indicating detection of the subsurface feature 14 of interest.

Turning now to a discussion of the portion of scanner 10 that defines the location of the subsurface feature 14, as shown in the embodiment depicted in FIGS. 1 and 2, a pair of journalled axles 70 are received by bearings (not shown) in housing 16. Wheels 72 are provided on each end of axles 70 for rolling contact with surface 12. In this manner, a relatively low-friction contact is provided between scanner 10 and surface 12, allowing it to be easily moved across surface 12. In addition, wheels 72 provide a uniform spacing between detector array 42 and surface 12 during operation. An optical encoder 74 is located adjacent, and driven by, the rear axle 70. The optical encoder 74 produces a position pulse for each predetermined angle of rotation described by axles 70 and wheels 72 that is calibrated with respect to wheel 72 diameter to correspond to linear displacement. Thus, as shown in FIG. 4, the output of optical encoder 74 can be supplied to a position counter 76, which displays the distance traveled by scanner 10 from an initial reference position.

The output of optical encoder 74 is also provided to a tachometer circuit 78, which produces a signal indicative of the speed at which scanner 10 is moving across surface 12. The output of tachometer circuit 78 is supplied to a heater interlock circuit 80, connected between heat source 20 and AC power supply 82. Interlock circuit 80 maintains a closed circuit to heat source 20 when tachometer circuit 78 indicates that scanner 10 is moving across surface 12. If, on the other hand, the output of tachometer circuit 78 indicates that scanner 10 is at rest, the power supplied to heat source 20 is interrupted, thereby preventing an undesirable build-up of heat at one point on surface 12. An additional input to interlock circuit 80 can be provided by a temperature limit switch, which responds to the temperature of surface 12 and causes interlock 80 to deactivate heat source 20 in the event an undesirably high surface temperature is reached.

Although not included in the preferred embodiment of the invention, a motor assembly could be used to drive one of the axles 70 to maintain a constant speed of scanner 10 across surface 12. In the preferred embodiment, such an assembly is eliminated as adding unnecessary weight to scanner 10, making it less suitable for hand-held use.

As shown in FIGS. 1 and 4, a number of outputs are provide on, and made available by, scanner 10 for operator consideration. For example, a row of light-emitting diode (LED) feature indicators 84 is recessed in the upper surface 40 of housing 16. In the apparatus depicted in FIGS. 1 and 2, eighteen LEDs 84 are positioned in the longitudinal line of, and substantially directly above, corresponding pyroelectric detectors 44 recessed in the lower surface 28 of housing 16. LEDs 84 are connected to the output of signal-conditioning circuit 58. As will be shown in greater detail below, LEDs 84 indicate whether particular subsurface feature types are being sensed by the associated pyroelectric detectors 44. Thus, both the type of subsurface feature 14 detected and its lateral position with respect to scanner 10 are indicated.

To determine the position of a detected defect along the direction of scanner 10 travel, the output of the position counter 76 provided on the upper surface 40 of housing 16 is read. The output of counter 76 indicates the longitudinal displacement of scanner 10 from an initial reference point and can be set up to directly indicate the longitudinal position of scanner 10 in any units of length desired. Thus, both the identity and location of subsurface features 14 are provided in real-time.

A row of Led speed indicators 86 is also provided on upper surface 40 of housing 16. These LEDs 86 are connected to the output of tachometer circuit 78 and display the relative speed of scanner 10 with respect to surface 12. Thus, for example, four LED indicators 86 may be employed with the forwardmost indicator 86 indicating relatively "fast" motion of scanner 10 with respect to some arbitrary reference speed and the rearwardmost LED indicator 86 indicating a relataively "slow" speed.

If desired, as shown in FIG. 4, the data produced by scanner 10 can be provided in digital form to data storage and output equipment 88. In a preferred embodiment, 20 channels of data, including one for each detector 44, one for position, and one for reset, are output to data storage equipment 88. There, the information is stored and can be retrieved and edited at the operator's convenience for post-test analysis. In addition, hard-copy outputs can be produced, such as profile plots indicating the output levels of eighteen detectors 44 as a function of longitudinal displacement or two-dimensional maps of the region of surface 12 scanned.

The remaining elements of scanner 10 will not be considered in conjunction with a discussion of the operation of scanner 10. Before scanner 10 is used to analyze surface 12, several preliminary steps are taken. For example, 120-volt AC power is input to a receptacle 92 provided on the upper surface 40 of housing 16. A portion of the AC input is used directly by scanner 10 to operate heat source 20. The remainder is used to produce DC power at DC power supply 93, for use by a number of components of scanner 10. The use of off-board AC power is preferred over an onboard power source because of the additional weight and space added to scanner 10 by an onboard source.

Next, a 20-channel data bus is attached to a connector 90 provided on the upper surface 40 of housing 16 to transfer data produced by scanner 10 to data storage and output equipment 88. Alternatively, the data produced by scanner 10 can be stored in onboard memory while it is being produced and, after surface 12 has been scanned, the data bus can be attached to connector 90 and information transferred to the data storage and output equipment 88.

A reset button 94 is pushed to reset the output of position counter 76 to zero. By aligning a reference point on scanner 10 with a reference point on surface 12 (for example, marked in chalk) at this time, subsequent outputs of position counter 76 can be used to indicate the distance traveled by scanner 10 along surface 12 and, hence, its longitudinal position with respect to surface 12. Adjustment knobs 56 are turned to provide the desired displacement between detector array 42 and surface 12.

At this time, the operator grasps a pair of handles 96 placed on opposite sides of upper surface 40 of scanner housing 16. Selector switch 63 is used to select the filter 60 or 62 to be used and, hence, the subsurface feature type to be detected. AC power switch 98 is then placed on its ON position, providing power to the heat source 20 and DC power supply 93. Similarly, DC power switch 100 is moved to its ON position, providing 12-volt DC power to components of scanner 10, including detectors 44 and signal-conditioning circuit 58. If a heat source 20 is to be employed, both heater power switch 102 and fan switch 104 are moved to their ON positions.

At this time, the operator begins to move scanner 10 across surface 12. As scanner 10 is progressed, position counter 76 produces an indication of the relative position of scanner 10 with respect to a referential starting point. LED indicators 86 provide the operator with an indication of the relative speed of scanner 10. Thus, the operator can maintain a substantially constant speed of scanner 10, eliminating the influence variations in speed might have on the output of detectors 44.

As the forward motion of scanner 10 continues, the operator views the LED feature indicators 84. If subsurface features 14 are encountered by one or more detectors 44, the corresponding LEDs 84 above the subsurface feature 14 are lit, indicating the presence of the feature type sought. Thus, the operator will be apprised of the location of a particular feature type with respect to surface 12. If desired, the operator can either mark the surface at this time or continue on and produce a map from data storage and output equipment 88 at a later date.

In a preferred embodiment, surface 12 may be initially scanned at a relatively high speed with heat source 20 on and switch 63 in a first position to identify and locate smaller subsurface features 14. Then, surface 12 is scanned again at a slower speed with heat source 20 off and switch 63 repositioned to identify larger subsurface features 14. The time delay between scans allows the heat produced by source 20 to flow through a broader region of surface 12. Thus, the surface temperature gradients produced by larger subsurface features 14 become more pronounced, making such features easier to detect.

As will be readily apparent, a scanner 10 constructed in the foregoing manner employs a method of identifying and locating subsurface features that is also a part of the present invention. This method, expressed in detail in the foregoing paragraphs with respect to the description of scanner 10, includes an initial step of exposing at least a portion of the surface to a uniform source of heat, either from its environment or an independent heat source. The temperature of the surface is then detected as a function of surface position or location and compared with surface temperatures corresponding to particular subsurface features of interest. When this comparison indicates that one of the subsurface features of interest is present, an indication is produced of the subsurface feature type, as well as its location with respect to the surface.

Those skilled in the art will recognize that the embodiments of the invention disclosed herein are exemplary in nature and that various changes can be made without departing from the scope and the spirit of the invention. In this regard, and as was previously mentioned, the invention can employ detectors that respond either directly or indirectly to the change in temperature of the surface. In addition, an auxiliary heat source can be employed or omitted, as desired. Similarly, the conditioning circuitry and form of output employed can be varied, pursuant to readily understood principles. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. An apparatus, for nondestructively locating and identifying features beneath a surface, comprising:
   detection means, responsive to the temperature of said surface, for producing an output when exposed to said surface, said output being a function of said temperature of said surface;
   location means for producing an indication of the relative position of said detection means with respect to said surface; and
   analyzing means for receiving said output of said detection means and said indication from said location means and for producing a response when said output falls within one of a plurality of predetermined output ranges associated with said features to be identified, each of said predetermined ranges corresponding to a particular type of said feature, said analyzing means including a filter that establishes said predetermined output range and passes said output of said detection means if said output falls within said one of said predetermined ranges, said response identifying said feature type associated with said one of said predetermined ranges and said relative position of said feature with respect to said surface.

2. The apparatus of claim 1, wherein said function relating said output of said detection means to said temperature of said surface is the change in said temperature between contiguous portions of said surface.

3. The apparatus of claim 1, wherein said analyzing means comprises a microprocessor.

4. the apparatus of claim 1, wherein said detection means comprises an array of pyroelectric detectors.

5. The apparatus of claim 4, further comprising a heat source for providing predetermined amounts of energy to said surface, said heat source being substantially parallel to said array of detectors and of substantially the same length as said array.

6. The apparatus of claim 5, further comprising means for displaying the location and identity of said features beneath said surface.

7. The apparatus of claim 6, wherein said means for displaying the location and identity of said features comprises an array of light-emitting diodes.

8. The apparatus of claim 7, wherein said means for displaying the location and identity of said features further comprises:
   means for storing information about said response of said analyzing means; and
   means for plotting said information about said response of said analyzing means.

9. The apparatus of claim 5, wherein said location means comprises means for producing a signal that is proportional to the relative motion between said apparatus and said surface.

10. The apparatus of claim 9, wherein said location means further comprises means for converting said signal proportional to said relative motion into an indication of the speed at which said apparatus is moving along said surface.

11. The apparatus of claim 9, wherein said location means further comprises means for extracting the location of said apparatus, with respect to a reference point on said surface, from said signal proportional to said relative motion between said apparatus and said surface.

12. The apparatus of claim 9, further comprising means for disabling said heat source when said signal proportional to the relative motion between said apparatus and said surface is substantially zero.

13. The apparatus of claim 4, further comprising means for adjusting the distance between said array of pyroelectric detectors and said surface.

14. The apparatus of claim 5, further comprising means for controlling the resolution of said pyroelectric detectors.

15. The apparatus of claim 5, further comprising means for shielding said linear array of pyroelectric detectors from direct exposure to said energy provided by said heat source.

16. A method of nondestructively locating and identifying features beneath a surface comprising the steps of:
   producing signals indicative of the temperature of a point on said surface and the location of said point with respect to said surface;
   filtering said signal indicative of the temperature of said point to determine whether said signal falls within a predetermined range associated with a particular type of said feature; and
   producing an indication if said step of filtering determines that said signal is within said predetermined range associated with said particular type of feature, said indication identifying said particular type of said feature present and said point on said surface at which said feature was detected.

17. The method of claim 16, wherein said step of producing said signal indicative of the temperature of said point comprises passing a linear array of pyroelectric detectors over said surface.

18. The method of claim 16, further comprising the step of uniformly heating said surface.

19. The method of claim 18, wherein said step of uniformly heating said surface comprises passing a heat source over said surface in spaced relation to said linear array of pyroelectric detectors.

* * * * *